United States Patent [19]

Kojimoto et al.

[11] Patent Number: 5,290,312
[45] Date of Patent: Mar. 1, 1994

[54] ARTIFICIAL VERTEBRAL BODY

[75] Inventors: Haruo Kojimoto, Tokyo; Natsuo Yasui, Osaka, both of Japan

[73] Assignee: Alphatec, Palm Desert, Calif.

[21] Appl. No.: 753,786

[22] Filed: Sep. 3, 1991

[51] Int. Cl.$^5$ .............................................. A61F 2/44
[52] U.S. Cl. ........................................ 623/17; 606/61
[58] Field of Search ................ 623/17; 606/61, 62, 606/63, 64, 60

[56] References Cited

U.S. PATENT DOCUMENTS

| | | | |
|---|---|---|---|
| 4,599,086 | 7/1986 | Doty | 623/17 |
| 4,834,757 | 5/1989 | Brantigan | 623/17 |
| 5,062,850 | 11/1991 | MacMillan et al. | 623/17 |
| 5,147,402 | 9/1992 | Bohler et al. | 623/16 |

FOREIGN PATENT DOCUMENTS

| | | | |
|---|---|---|---|
| 0188954 | 7/1986 | European Pat. Off. | 623/17 |
| 2636227 | 3/1990 | France | 623/17 |
| 1560184 | 4/1990 | U.S.S.R. | 623/17 |

*Primary Examiner*—David Isabella
*Assistant Examiner*—Debra S. Brittingham
*Attorney, Agent, or Firm*—Knobbe, Martens, Olson & Bear

[57] ABSTRACT

A prosthetic vertebra has a first hollow parallelepiped-shaped component and a second component shaped identically to the first component and marginally smaller than the first component. The second component can accordingly be positioned partially within the first component and can be axially moved within the first component, so that the overall length of the prosthetic vertebra can be established by appropriately moving the second component within the first. A set screw is threadably engageable with the first component and can be tightened against the second component to hold the components axially stationary relative to each other, once the prosthetic vertebra has been positioned in the patient and its length adjusted as appropriate to fit the patient.

15 Claims, 3 Drawing Sheets

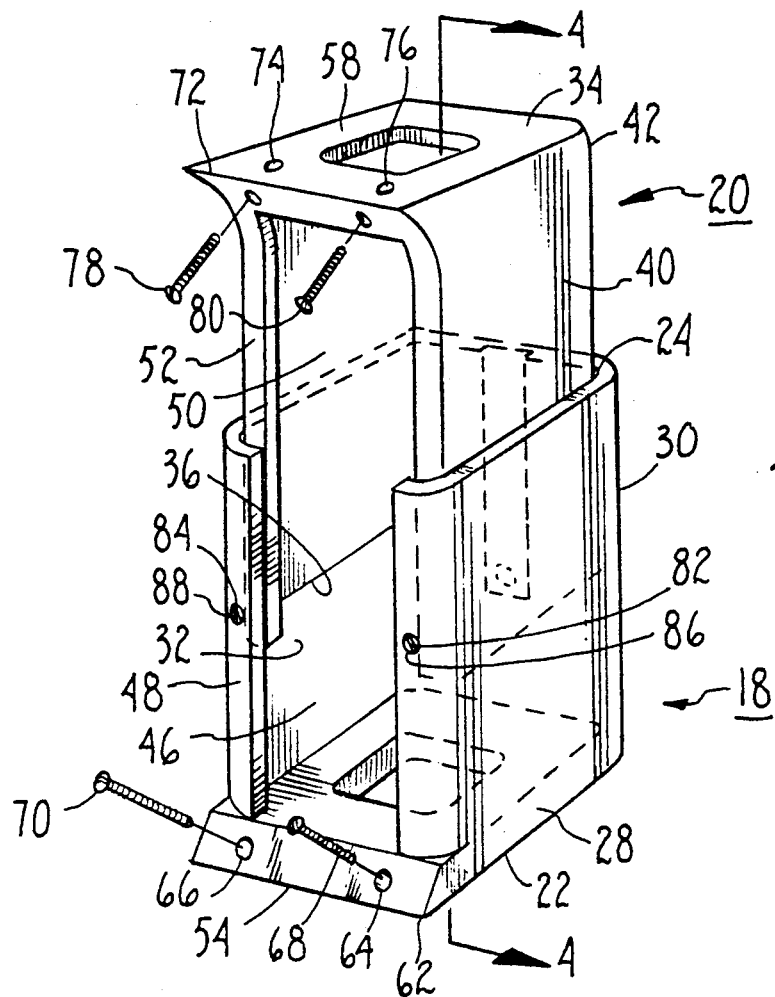
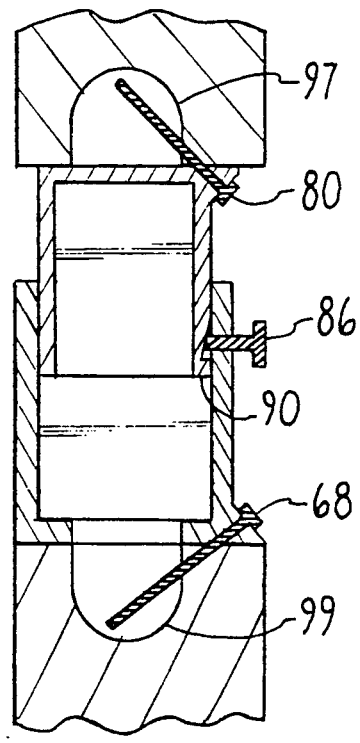

ARTIFICIAL VERTEBRAL BODY

FIELD OF THE INVENTION

The present invention relates generally to prosthetic devices. More particularly, the present invention relates to prosthetic devices for the back. The present invention particularly, but not exclusively, relates to artificial vertebra.

BACKGROUND

Patients who have relatively severe backbone disorders, such as cancerous metastasis of the spine, can experience ancillary disorders, such as severe spinal curvature, in addition to the metastasis. Certain of these ancillary disorders, e.g., severe curvature of the spine, can cause considerable patient discomfort and cause the patient to encounter paralysis or discomfort.

To alleviate the patient's condition, methods have been developed whereby a metastasized vertebra is removed from the spine, and a prosthetic vertebra is positioned in the spine in place of the removed metastasized vertebra. Typically, a prosthetic vertebra is a hollow ceramic cube which has several openings formed in the sides of the cube. After the metastasized vertebra has been removed, the upper portion of the spine is distracted away from the lower portion of the spine, and cavities are drilled into the vertebrae which are adjacent the space left by the removal of the metastasized vertebra. The prosthetic vertebra is then inserted into the space between the adjacent vertebrae.

After the prosthetic vertebra has been positioned in the patient, pliable bone cement is infused through one or more of the openings of the prosthetic vertebra to fill the hollow vertebra. Also, the pliable bone cement flows out of other openings in the cube and thence into the cavities which are drilled into the adjacent vertebrae. Fastening screws are positioned through the bone structure of the adjacent vertebrae and into the pliable bone cement. When the bone cement hardens, the screws fasten the bone cement (and, hence, the prosthetic vertebra) to the vertebrae that are adjacent to the prosthetic vertebra.

To effectively alleviate the spinal curvature, it is desirable that the prosthetic vertebra have the same dimensions as the removed vertebra had before it became metastasized, to maintain a predetermined distance between the adjacent vertebrae. Without the spacing effect of the prosthetic vertebra, the vertebrae that are adjacent to the area left by the removed metastasized vertebra would otherwise tend to move toward each other and thus worsen the curvature of the spine.

Not surprisingly, however, it is relatively rare for a prosthetic vertebrae of fixed size to exactly fit the space left by the removed metastasized vertebra between the adjacent vertebrae. Typically, therefore, a larger-than-needed prosthetic vertebra is used, and the surfaces of the adjacent vertebrae are scraped to provide sufficient space between the vertebrae for the prosthetic vertebra. In patients already suffering from other spinal debilities, such scraping undesirably weakens the vertebrae. Also, attaching the prosthetic vertebra to existing vertebra by means of screws which fasten the bone cement to the existing vertebrae may result in a relatively weak, brittle bond between the prosthetic vertebra and the patient's existing bone structure.

Furthermore, conventional techniques and apparatus for distracting the upper portion of the spine away from the lower portion of the spine can weaken existing bone structure and interfere with the procedure for inserting the prosthetic vertebra. More particularly, conventional techniques and apparatus require pressure to be applied to relatively weak edges of the vertebrae. Typically, the pressure is applied by means of a distractor having two legs pivotally connected together. One leg is engaged with the edge of one of the adjacent vertebrae, and the other leg is engaged with the edge of the other adjacent vertebra. The distractor is then mechanically manipulated to force the vertebrae away from each other. Unfortunately, the distractor, which must be left in place to permit insertion of the prosthetic device between the adjacent vertebrae, interferes with the insertion of the prosthetic vertebra. Also, the distractor may weaken, chip, or break portions of the adjacent vertebrae.

Accordingly, it is an object of the present invention to provide a prosthetic vertebra which can be fitted in vivo to a range of users. It is a further object of the present invention to provide a prosthetic vertebra which can be installed without unduly stressing the existing bone structure of the patient. Another object of the present invention is to provide a prosthetic vertebra which can be reliably connected to the existing bone structure of the patient. Yet another object of the present invention is to provide a prosthetic vertebra which is easy to use and cost-effective to manufacture.

SUMMARY OF THE INVENTION

A prosthetic vertebra is provided for replacing a metastasized vertebra. Typically, the metastasized vertebra will have been removed from a location in a patient's spine which is between adjacent first and second vertebrae. The prosthetic vertebra has a first component engageable with the first vertebra and a second component engageable with the second vertebra. The second component is slidably engageable with the first component to establish a prosthetic vertebra having an adjustable length. Means are provided for preventing slidable motion between the components to establish the length of the prosthetic vertebra to be substantially equal to a desired predetermined distance between the first and second vertebrae.

In a preferred embodiment, the components are shaped essentially identically, with the second component being slightly smaller than the first to permit the second component to slide within the first component. Accordingly, when the components are slidably engaged, the components are coaxial.

Preferably, each component is configured as a hollow, slightly elongated parallelepiped, and each has an abutting end surface for abutting a vertebra of a living being and an anchoring window centrally formed in the abutting end surface. Also, each component has an open first side which establishes an access window, and an open end formed opposite the abutting end.

In accordance with the preferred embodiment, the open end of the second component is slidably receivable through the open end of the first component. Thus, the abutting end of one component can be engaged with the first vertebra and when so engaged is accordingly oriented toward the patient's head. On the other hand, the abutting end of the other component can be engaged with the second vertebra and when so engaged is accordingly oriented toward the patient's feet.

The open side of each component is essentially a lip, and the lip partially surrounds the access window of the open side of each component. In a preferred embodiment, the means for preventing motion between the components includes a screw, and the lip of the first component has a hole formed in it for receiving the screw. The screw is threadably engageable with the hole and can be rotated to abut the lip of the second component. When the screw is tightened against the lip of the second component, the screw holds the second component stationary with respect to the first component.

If desired, a channel can be formed in the lip of the second component, and the channel has a first end located near the abutting end of the second component and a second end located near the open end of the second component. The channel has a bottom wall, and the bottom wall tapers upwardly toward the surface of the lip from the second end of the channel to the first end of the channel. When the screw is tightened, the screw abuts the bottom wall of the channel. Accordingly, the tapered configuration of the bottom wall inhibits slidable motion between the screw and bottom wall which may be caused by compressive forces exerted by the patient's body on the prosthetic vertebra.

The prosthetic vertebra of the present invention also includes means engageable with each component to fixedly anchor the component to one of the patient's vertebra. In a preferred embodiment, the abutting end of each component is formed with a flange, and the anchoring means for each component includes two bolts which can be threadably engaged with a respective aperture formed in the flange. The bolts can be tightened to threadably engage the vertebra to which the component is to be anchored.

Preferably, to provide greater structural strength between the prosthetic vertebra and the patient, each aperture defines a longitudinal axis, and the longitudinal axis of each aperture establishes an oblique angle with the longitudinal axis of the component. Thus, the bolts are oriented at an oblique angle relative to the spinal axis and are accordingly less likely to become detached from the vertebral bone during periods of tensile stress or shear.

In another aspect of the present invention, an artificial vertebra is provided which is positionable between a first and second vertebra to establish a predetermined distance therebetween. The artificial vertebra includes a first hollow component and a second hollow component. Each component is generally shaped as an elongated parallelepiped having an open end and an abutting end having an abutting end surface for abutting a vertebra. An anchoring window is formed in the abutting end surface of each component, and each component has first, second, and third closed sides extending between the abutting and open ends and an open fourth side having an access window formed therein. The open fourth side is essentially a lip, and an access window is bounded by the lip. The open end of the second component is slidably receivable through the open end of the first component to establish an adjustable length of the artificial vertebra.

To prevent relative motion between the components, a hole is formed in the lip of the open side of the first component, and a screw is engaged with the hole to abut the second component. A predetermined length for the artificial vertebra is thereby established to be approximately equal to a desired predetermined distance between the first and second vertebrae. Further, an aperture is formed in the abutting end surface of each component, and a bolt is engaged with each aperture and the respective vertebra to hold the component against the vertebra.

In yet another aspect of the present invention, a method is disclosed for replacing a metastatic vertebra located between a first and a second vertebra of a patient. The method includes the steps of removing the metastatic vertebra from the patient, and then drilling cavities into the vertebrae which are adjacent to the space left by the removed vertebra. The adjacent vertebrae, however, do not have to be filed to fit the artificial vertebra of the present invention. Instead, the artificial vertebra is positioned between the upper and lower spinal portions, and the artificial vertebra is distracted as necessary.

More particularly, the artificial vertebra includes a first component and a second component, and the components are slidably engaged with each other so that they can be distracted away from each other. Accordingly, when the artificial vertebra has been positioned as desired, the first component is distracted relative to the second component to establish the length of the artificial vertebra. Preferably, the length of the artificial vertebra is established to be substantially equal to a predetermined desired distance between the vertebrae which are adjacent to the artificial vertebra.

Upon establishing the predetermined length of the artificial vertebra, relative motion is prevented between the first and second components. Stated differently, the first and second components are axially locked together when the predetermined length has been established. Then, the first and second components are respectively connected to the first and second vertebrae. This is accomplished by infusing pliable bone cement into the components through access windows formed in the components. Cement flows out of anchor windows formed in the components and into the cavities of the vertebrae adjacent to the artificial vertebra. Before the cement hardens, bolts are engaged with each component and its associated adjacent vertebra, and each bolt extends into the pliable cement within the vertebral cavity. When the cement hardens, the artificial vertebra is fixedly connected to the spine between the vertebrae that are adjacent the artificial vertebra.

The present invention summarized above can best be understood in reference to the accompanying drawings, in which like numerals refer to like parts, the drawings being briefly described below.

BRIEF DESCRIPTION OF THE DRAWINGS

FIG. 3 is a perspective view of the prosthetic vertebra of the present invention shown in FIG. 1, with the components engaged, and with portions shown in phantom;

FIG. 4 is a cross-sectional view of the prosthetic vertebra of the present invention, as seen along the line 4—4 in FIG. 3;

DETAILED DESCRIPTION OF THE PREFERRED EMBODIMENTS

Figures 1, 2:
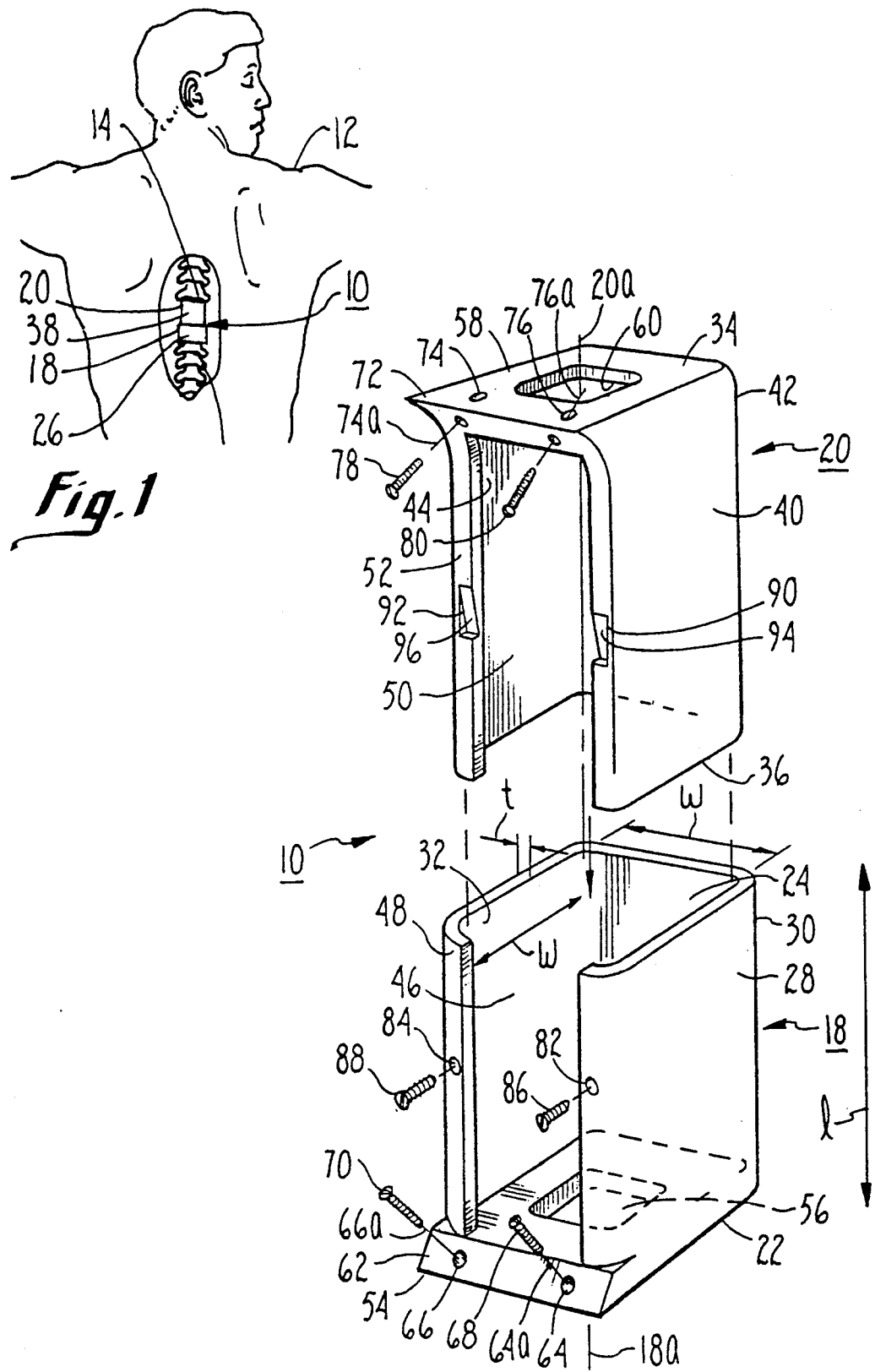
FIG. 1 is a perspective view of the prosthetic vertebra of the present invention, shown in its intended environment.
FIG. 2 is a perspective view of the prosthetic vertebra of the present invention shown in FIG. 1, with the components disengaged, and with portions shown in phantom.

Referring initially to FIG. 1, a prosthetic vertebra is shown, generally designated 10. As shown, the prosthetic vertebra 10 is positioned within a patient 12 between two spinal vertebrae 14, 16 of the patient 12. It is to be understood in reference to FIG. 1 that a metastasized vertebra (not shown) has been removed from between the vertebrae 14, 16, and that the prosthetic vertebra 10 has been positioned within the patient 12 in place of the metastasized vertebra, in accordance with the disclosure below.

Now referring to FIGS. 2 and 3, the details of the prosthetic vertebra 10 can be seen. In accordance with the present invention, the prosthetic vertebra 10 is cast or machined from titanium, although other strong, biologically-compatible materials can be used. For example, the prosthetic vertebra 10 can be made of stainless steel or ceramic.

As shown in FIGS. 2 and 3, the prosthetic vertebra 10 includes a first component generally designated 18 and a second component generally designated 20. As shown, the components 18, 20 are shaped substantially identically. The second component 20, however, is slightly smaller than the first component 18, to permit the second component 20 to slide within the first component 18.

In the embodiment shown in FIGS. 2 and 3, the components 18, 20 are hollow, and are substantially shaped as slightly elongated parallelepipeds. Thus, the first component 18 defines a longitudinal axis 18a, and has an abutting end 22, an opposing open end 24, and first, second, third, and fourth sides 48, 28, 30, 32. As shown, the first and third sides 48 and 30 are orthogonal to the second and fourth sides 28, 32. Also, all four sides 48, 28, 30, 32 are orthogonal to the ends 22, 24. FIGS. 2 and 3 show that the corners between the sides 48, 28, 30, 32 are gently rounded, and not sharp, to prevent damage to the tissue of the patient which surrounds the prosthetic vertebra 10 when the vertebra 10 is installed in the patient 12.

Similarly, the second component 20 defines a longitudinal axis 20a, and has an abutting end 34, an opposing open end 36, and first, second, third, and fourth sides 52, 40, 42, 44. As shown, the first and third sides 52 and 42 are orthogonal to the second and fourth sides 40, 44. Also, all four sides 52, 40, 42, 44 are orthogonal to the ends 34, 36 of the second component 20. FIGS. 2 and 3 show that the corners between the sides 52, 40, 42, 44, like the corners between the sides 48, 28, 30, 32 of the first component 18, are gently rounded, and not sharp. Also, as shown best in FIG. 3, when the components 18, 20 are slidably engaged, the axes 18a, 20a are coincident. In other words, the components 18, 20 are coaxially engaged.

FIGS. 2 and 3 show that the second, third, and fourth sides 28, 30, 32 of the first component 18 are closed. Similarly, the second, third, and fourth sides 40, 42, 44 of the second component 20 are closed. On the other hand, the first sides 48, 52 of the first and second components 18, 20 are open, and are essentially defined by a narrow lip. More particularly, an access window 46 is formed in the first side 48 of the first component 18, and the first side 48 partially surrounds the access window 46. As shown in FIGS. 2 and 3, the first side 48 is orthogonally oriented with respect to the second and fourth sides 28, 32 of the first component 18.

Likewise, an access window 50 is formed in the first side 52 of the second component 20, and the first side 52 is essentially a lip that partially surrounds the access window 50. As shown in FIGS. 2 and 3, the first side 52 is orthogonally oriented with respect to the second and fourth sides 40, 44 of the second component 20.

Still referring to FIGS. 2 and 3, the abutting end 22 of the first component 18 includes an abutting end surface 54 which can abut the vertebra 14. A generally square anchor window 56 is formed substantially in the middle of the abutting end surface 54. Also, the abutting end 34 of the second component 20 includes an abutting end surface 58 which can abut the vertebra 16, and an access window 60 is formed substantially in the middle of the abutting end surface 58.

The abutting end surface 54 of the first component 18 includes a flanged portion 62 which extends outwardly from the abutting end surface 54. As shown in FIGS. 2 and 3, at least one, and preferably two, threaded apertures 64, 66 are drilled through the flanged portion 62. If desired, even more apertures (not shown) may be drilled into the flanged portion 62. FIG. 3 shows that threaded bolts 68, 70 can be threadably engaged with apertures 64, 66 for purposes more fully disclosed below. FIGS. 2 and 3 show that the respective longitudinal axes 64a, 66a of the apertures 64, 66 are oriented at an oblique angle relative to the axis 18a of the first component 18.

FIGS. 2 and 3 further show that the abutting end surface 58 of the second component 20 includes a flanged portion 72 which extends outwardly from the abutting end surface 58. As shown in FIGS. 2 and 3, at least one, and preferably two, threaded apertures 74, 76 are drilled through the flanged portion 72. If desired, even more apertures (not shown) may be drilled into the flanged portion 72. Threaded bolts 78, 80 (FIG. 3) can be threadably engaged with apertures 74, 76 for purposes more fully disclosed below. FIGS. 2 and 3 show that the respective longitudinal axes 74a, 76a of the apertures 74, 76 are oriented at an oblique angle relative to the axis 20a of the second component 20.

In contrast to the abutting ends 22, 34, the open ends 24, 36 of the components 18, 20 do not include surface portions similar to the surfaces 54, 58, but are instead open. In accordance with the present invention, the open end 36 of the second component 20 is receivable through the open end 24 of the first component 18.

FIGS. 2 and 3 further show that two holes 82, 84 are formed through the first side 48 of the first component 18. Preferably, the holes 82, 84 are threaded. As best shown in FIG. 4, a screw 86 can be threadably engaged with the hole 82 to abut the first side 52 of the second component 20. Also, a screw 88 can be threadably engaged with the hole 84 to abut the first side 52 of the second component 20. When the screws 86, 88 are tightened against the first side 52 of the second component 20, relative axial motion is prevented between the components 18, 20. Stated differently, the screws 86, 88 can be tightened to hold, by friction, the second component 20 against the screws 86, 88 (and, hence, the first component 18).

Referring back to FIG. 2, two channels 90, 92 can, if desired, be formed on the first side 52 of the second component 20. As shown, the first channel 90 has a bottom wall 94, and the second channel 92 has a bottom wall 96. Each of the walls 94, 96 is tapered upwardly toward the surface of the first side 52 from the end of the channel 90, 92 that is nearer to the open end 36 of the second component 20 to the end of the channel 90, 92 that is nearer to the abutting end 34 of the second component 20. Thus, in the embodiment wherein the channels 90, 92 are formed in the first side 52, the screws 86, 88 abut the bottom walls 94, 96 of the channels 90, 92. Accordingly, the skilled artisan will appreciate that because of their tapered bottom walls 94, 96, the channels 90, 92 augment the frictional holding force between the screws 90, 92 and the second component 20.

While FIGS. 2 and 3 show that the components 18, 20 of the prosthetic vertebra 10 are shaped as parallelepipeds, it is to be understood that the components 18, 20 may have three, five, six, or more sides (not shown), as long as the components 18, 20 are prevented from rotating relative to each other when the components 18, 20 are engaged.

Moreover, although the prosthetic vertebra 10 can be made in various sizes, as appropriate for the particular patient 12, in one presently preferred embodiment each side of the first component 18 of the prosthetic vertebra 10 has a thickness "t" of about five one-hundredths of an inch (0.05"), a length "l" of about three quarters of an inch (0.75"), and a width "w" of about one half of an inch (0.5"). As disclosed above, the sides of the second component 20 are slightly smaller than the sides of the first component 18.

Figures 5, 6:
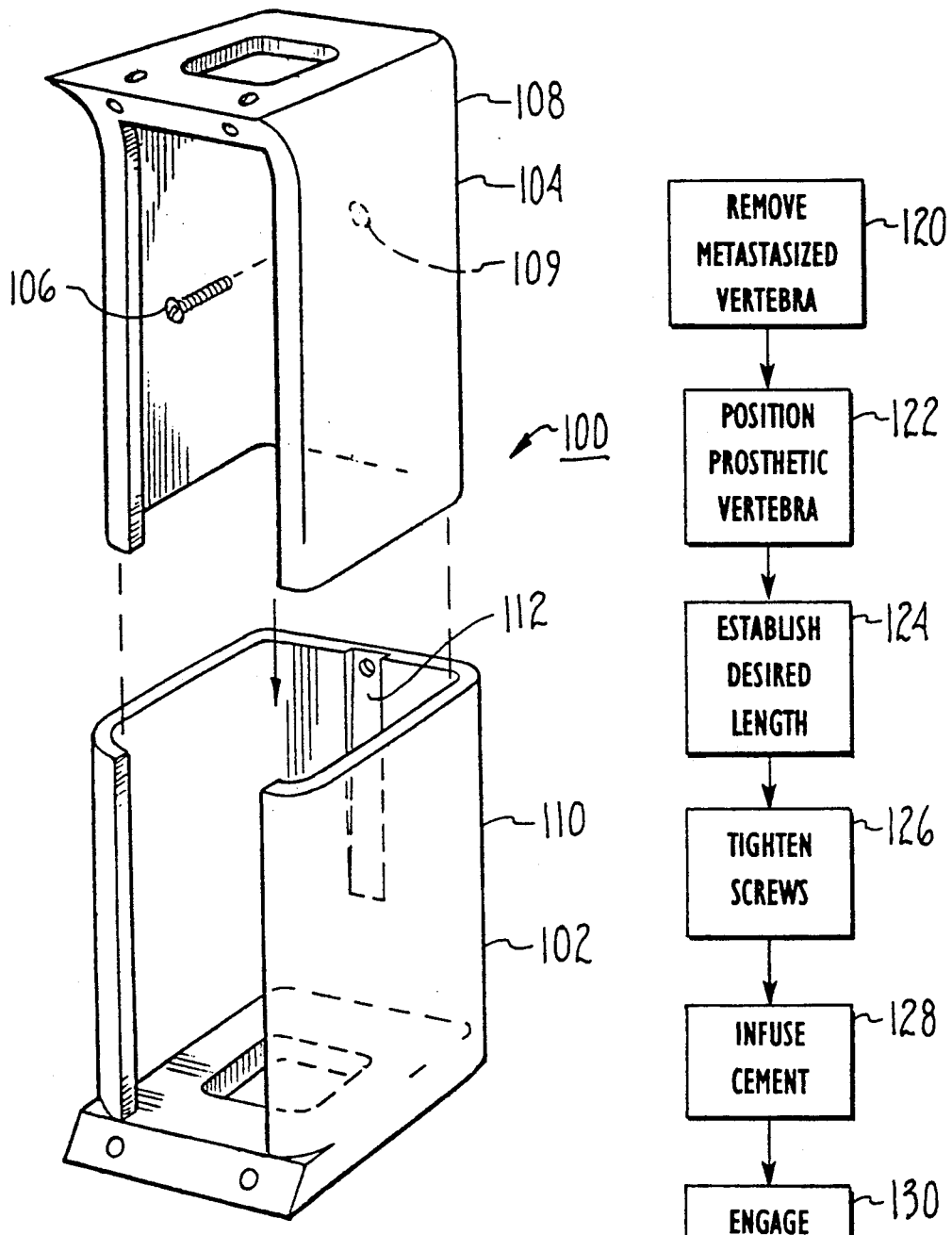
FIG. 5 is a perspective view of an alternative embodiment of the prosthetic vertebra of the present invention, with the components disengaged, and with portions shown in phantom.
FIG. 6 is a block diagram of the method for replacing a metastasized vertebra with the prosthetic vertebra of the present invention.

Now referring to FIG. 5, and alternative embodiment of the prosthetic vertebra of the present invention is shown, generally designated 100. As shown, the prosthetic vertebra 100 is in all essential respects identical to the prosthetic vertebra 10, except that the prosthetic vertebra 100 has a first component 102 and a second component 104 which are held axially stationary with respect to each other by a screw 106 that is engaged with second sides 108, 110 of the components 102, 104.

More particularly, as can be appreciated in reference to FIG. 5, the screw 106 can be threadably engaged with a hole 109 that is formed in the second side 110 of the second component 104. The screw 106 can be tightened to abut the second side 108 of the first component 102 to prevent relative axial motion between the components 102, 104. If desired, a channel 112 having a tapered bottom wall can be formed in the second side 108 of the first component 102, to function like the channels 90, 92 in the prosthetic vertebra 10.

In the operation of the prosthetic device 10, cross-reference is made to FIGS. 1-4 and 6. As indicated at block 120 in FIG. 6, a metastasized or otherwise diseased or damaged vertebra is first removed from the patient 12. After removal of the diseased vertebra, cavities 97, 99 are drilled or otherwise formed in the vertebrae 14, 16.

Then, as indicated at block 122, the prosthetic vertebra 10, with the screws 86, 88 engaged with the holes 82, 84 but not tightened against the first side 52, is positioned between the vertebrae 14, 16 which are adjacent to the space left by the removed metastasized vertebra. As can be appreciated in cross-reference to FIGS. 1 and 3, when the prosthetic vertebra 10 is properly positioned, the abutting end surface 58 of the second component 20 abuts the vertebra 14. Also, the abutting end surface 54 of the first component 18 abuts the vertebra 16. Thus, when the prosthetic vertebra 10 is properly positioned, the abutting end 22 of the first 10 component 18 is oriented toward the feet of the patient 12, while the abutting end 34 of the second component 20 is oriented toward the head of the patient 12. Further, when the prosthetic vertebra 10 is properly positioned, the first sides 26, 38 of the components 18, 20 are the anterior sides of the prosthetic vertebra 10.

Block 124 indicates that the components 18, 20 of the prosthetic vertebra 10 are next moved axially relative to each other to establish a predetermined length of the prosthetic vertebra 10. Preferably, the predetermined length of the vertebra 10 is established to be equal to a desired predetermined distance between the vertebrae 14, 16. Typically, the desired predetermined distance will be equal to the length that the removed vertebra had before it became damaged or diseased. The components 18, 20 may be urged away from each other to establish the predetermined length by any suitable means, such as by engaging a distractor with the components 18, 20 and distracting the components. Thus, the vertebrae 14, 16 are not moved apart by direct contact with a distractor (and, hence, are not potentially damaged).

After the predetermined length for the prosthetic vertebra 10 has been established as described, block 126 indicates that the screws 86, 88 are rotated and tightened against the first side 52 to prevent further axial relative motion between the components 18, 20. Because the first sides 26, 38 of the prosthetic vertebra 10 are the anterior sides, there is open access to the screws 86, 88.

Next, block 128 indicates that a suitable pliable bone cement (not shown) such as Simplex Bone Cement manufactured by Howmedia Inc. of Rutherford, N.J. is infused into the access windows 46, 50 of the components 18, 20 of the prosthetic vertebra 10. This cement flows into the chambers formed by the components 18, 20 and also flows through the anchor windows 56, 60 of the components 18, 20 into the cavities 97, 99. As indicated at block 130 and shown best in FIG. 4, the bolts 68 and 70 are engaged with the apertures 64, 66 and are also positioned through the vertebra 16 and into the still-pliable cement within the cavity 99. The bolts 68, 70 may be positioned through pre-drilled holes in the vertebra 16, or the bolts 68, 70 may be self-tapping.

Similarly, the bolts 78 and 80 are engaged with the apertures 74, 76 and are also positioned through the vertebra 14 and into the still-pliable cement within the cavity 97. The bolts 78, 80 may be positioned through pre-drilled holes in the vertebra 14, or the bolts 78, 80 may be self-tapping.

When the cement within the cavities 97, 99 hardens, the bolts 68, 70, 78, 80 hold the prosthetic vertebra 10 firmly against the vertebrae 14, 16.

It is to be appreciated in reference to the above disclosure that the present invention provides a prosthetic vertebra which can be precisely fitted in vivo in the spine of a patient, without requiring the grinding away of portions of the patient's existing vertebrae. Further, the present invention provides a prosthetic vertebra that can be held firmly onto existing vertebrae of the patient, and which does not solely rely on a cement bond to hold the prosthetic vertebra in place. In other words, the bond provided by the bolts 68, 70, 78, 80, in combination with the bone cement, establish a comparatively stronger and more reliable bond than is provided by prior art devices in which the bolts do not pass through the prosthetic device itself.

While the embodiments described above are fully capable of meeting the objects of the present invention, it is to be understood that the scope of the present invention is to be limited by nothing other than the limitations recited in the appended claims.

We claim:

1. An implantable artificial vertebra which is biocompatible and sized for replacing a metastatic vertebra, comprising:
    a first hollow component having an abutting end for abutting a vertebra of a living being and an anchoring window formed in said abutting end, an open first side establishing an access window, and an open end formed opposite said abutting end;
    a second hollow component having a second abutting end for abutting a vertebra of a living being and a second anchoring window formed in said second abutting end, an open first side establishing a second access window, and a second open end formed opposite said second abutting end, the second component being slidably receivable through the open end of said first component; and
    motion preventing means engageable with both of said components for substantially preventing slidable motion between said components.

2. The artificial vertebra recited in claim 1, wherein each component is shaped generally as an elongated parallelepiped.

3. The artificial vertebra recited in claim 2, wherein each abutting end includes an abutting end surface for abutting a vertebra of a living being, and each anchoring window is formed in its respective abutting end to establish a passageway through the abutting end surface for infusing bone cement therethrough.

4. The artificial vertebra recited in claim 3, wherein each component has four sides, said first side of each component having an access window formed therein, each first side comprising a lip surrounding a portion of said access window, the other three sides of each component being closed to form a chamber within each component.

5. The artificial vertebra recited in claim 4, wherein said motion preventing means includes a screw, and said lip of said first component has a hole formed therein for receiving said screw, said screw being threadably engageable with said hole to abut said second component and hold said second component stationary with respect to said screw.

6. The artificial vertebra recited in claim 5, wherein said second component has a channel formed therein, said channel having a tapered bottom wall, said screw being engageable with said hole in said first component to abut said channel.

7. The artificial vertebra recited in claim 1, further comprising anchoring means engageable with each said component to attach each component to a vertebra of a living being.

8. The artificial vertebra recited in claim 7, wherein said anchoring means for each component includes a bolt and flange formed on the abutting end surface of said component, said flange having an aperture formed therethrough, said bolt being engageable with said aperture and the vertebra of the living being to hold said component against the vertebra.

9. The artificial vertebra recited in claim 8, wherein each component defines a longitudinal axis extending through said abutting end and said open end, and said aperture has a longitudinal axis, said aperture being formed in said flange with the axis of said aperture establishing an oblique angle with the axis of said component.

10. A method for replacing a metastatic vertebra located between a first and a second vertebra of a patient, comprising;
    removing the metastatic vertebra from the patient;
    providing a first hollow component having an abutting end for abutting a vertebra of a living being and an anchoring window formed in said abutting end, an open first side establishing an access window, and an open end formed opposite said abutting end;
    providing a second hollow component having an abutting end, said second abutting end for abutting a vertebra of a living being and a second anchoring window formed in said second abutting end, an open first side establishing a second access window, and a second open end formed opposite said second abutting end, said components being slidably engaged with each other to establish an implantable artificial vertebra which is biocompatible and having an adjustable length;
    positioning said artificial vertebra between said first and second vertebrae;
    sliding the first hollow component relative to the second hollow component to establish the length of the artificial vertebra to be substantially equal to a predetermined distance between the first and second vertebrae;
    preventing relative motion between the first and second components; and
    respectively connecting the first and second components to the first and second vertebrae.

11. The method of claim 10, wherein each component is shaped generally as an elongated parallelepiped, wherein the second component is slidably receivable through the open end of said first component.

12. The method of claim 11, wherein each component forms a chamber and the abutting end of each component includes an abutting end surface for abutting a vertebra, and each anchoring window is formed in its respective abutting end to establish a passageway through the abutting end surface to the chamber.

13. The method of claim 12, wherein said connecting step comprises infusing bone cement into the access window of each component to fill each chamber and to flow through the anchoring windows and onto the first and second vertebrae.

14. The method of claim 13, wherein said connecting step further comprises:
    engaging a bolt with each component and the bone cement to hold the component against the vertebra.

15. An artificial implantable vertebra which is biocompatible and positionable between a first and second vertebra to establish a predetermined distance therebetween, comprising:
    a first and a second hollow component, each component generally shaped as an elongated parallelepiped having an open end and abutting end having an abutting end surface for abutting an associated vertebra and an anchoring window formed in said abutting end surface, each component having first, second, and third closed sides and an open side having an access window formed therein, said access window being bounded by a lip, and the second component being slidably receivable through the open end of the first component to establish an adjustable length of the artificial vertebra;

a hole formed in the lip of the open side of the first component;

a screw engageable with said hole to abut said second component to hold said second component stationary with respect to said first component and thereby establish a predetermined length for said artificial vertebra, said predetermined length being established to be approximately equal to the predetermined distance between the first and second vertebrae;

an aperture formed in the abutting end surface of each component; and a bolt engageable with each aperture and the associated vertebra to hold the component against the vertebra.

* * * * *